（12) United States Patent
Marble et al.

(10) Patent No.: US 8,593,144 B2
(45) Date of Patent: Nov. 26, 2013

(54) MAGNET ARRAY

(75) Inventors: Andrew E. Marble, Ottawa (CA);
Bruce J Balcom, Fredericton (CA);
Bruce Colpitts, Fredericton (CA); Igor V Mastikhin, Fredericton (CA)

(73) Assignee: University of New Brunswick, Fredericton, NB (CA)

( * ) Notice: Subject to any disclaimer, the term of this patent is extended or adjusted under 35 U.S.C. 154(b) by 927 days.

(21) Appl. No.: 12/516,321

(22) PCT Filed: Nov. 23, 2007

(86) PCT No.: PCT/CA2007/002115
§ 371 (c)(1),
(2), (4) Date: Feb. 8, 2010

(87) PCT Pub. No.: WO2008/061371
PCT Pub. Date: May 29, 2008

(65) Prior Publication Data
US 2010/0148777 A1    Jun. 17, 2010

Related U.S. Application Data

(60) Provisional application No. 60/860,809, filed on Nov. 24, 2006.

(51) Int. Cl.
*G01V 3/00* (2006.01)

(52) U.S. Cl.
USPC ............................................ 324/318; 324/309

(58) Field of Classification Search
USPC ........................... 324/300–322; 600/407–445
See application file for complete search history.

(56) References Cited

U.S. PATENT DOCUMENTS 3,213,357 A    10/1965  Brown et al.
4,350,955 A    9/1982   Jackson et al.

(Continued)

FOREIGN PATENT DOCUMENTS

CA    2344522    10/2001
CA    2416921    2/2002

(Continued)

OTHER PUBLICATIONS

J.A. Jackson, L. J. Burnett, J. F. Harmon, "Remote (inside-out) NMR, III. Detection of Nuclear Magnetic Resonance in a Remotely Produced Region of Homogeneous Magnetic Field," J. Magn. Res. 41, 1980, 411-421.

(Continued)

*Primary Examiner* — Brij Shrivastav
(74) *Attorney, Agent, or Firm* — Eugene F. Derényi; Fogler, Rubinoff LLP

(57) ABSTRACT

A magnet array is disclosed which is suitable for inter alia producing a remote field for use in unilateral magnetic resonance. In the "Magnet Array", two separated magnets, which are magnetized along a substantially same collinear magnetization direction, produce a field with a local maximum centered above and between them. The field produced by the two separated magnets is substantially parallel to the collinear magnetization direction of the two separated magnets. A third magnet is centered between the two separated magnets. The third magnet has a magnetization direction which is substantially parallel to the collinear magnetization direction of the two separated magnets. The third magnet produces a field which is substantially parallel to the collinear magnetization direction of the two separated magnets, and adds to the increasing field below the local maximum point produced by the two separated magnets. The field of the third magnet, which decays with distance, adds to the increasing field below the local maximum point. The position of the third magnet is selected in order to generate a total field which has at least one of its first and second spatial derivatives with respect to the distance above the magnet array substantially equal to zero.

20 Claims, 9 Drawing Sheets

(56) References Cited

U.S. PATENT DOCUMENTS

| | | | |
|---|---|---|---|
| 4,445,102 | A | 4/1984 | Thorn et al. |
| 4,810,965 | A * | 3/1989 | Fujiwara et al. ......... 324/207.22 |
| 5,572,132 | A | 11/1996 | Pulyer |
| 6,204,665 | B1 | 3/2001 | Triebe et al. |
| 6,489,872 | B1 | 12/2002 | Fukushima |
| 6,694,602 | B2 | 2/2004 | Laskaris et al. |
| 7,319,326 | B2 | 1/2008 | Balcom et al. |
| 7,352,179 | B2 | 4/2008 | Chen et al. |
| 7,404,667 | B2 * | 7/2008 | Born et al. .................... 368/190 |
| 7,567,079 | B2 | 7/2009 | Chen et al. |
| 7,721,740 | B2 * | 5/2010 | Boucher et al. .............. 128/848 |
| 7,733,091 | B2 | 6/2010 | Marble et al. |
| 8,047,206 | B2 * | 11/2011 | Boucher et al. .............. 128/848 |
| 2003/0218470 | A1 | 11/2003 | Pulyer |
| 2004/0066194 | A1 * | 4/2004 | Slade et al. .................. 324/318 |
| 2005/0128037 | A1 | 6/2005 | Doi et al. |
| 2006/0084861 | A1 * | 4/2006 | Blank et al. .................. 600/423 |
| 2012/0085613 | A1 * | 4/2012 | Bose et al. .................... 192/21.5 |
| 2012/0262261 | A1 * | 10/2012 | Sarai ............................ 335/306 |

FOREIGN PATENT DOCUMENTS

| | | |
|---|---|---|
| FR | 2 793 882 A1 | 11/2000 |
| GB | 2174247 | 10/1986 |
| WO | WO 93/14414 | 7/1993 |
| WO | WO 98/03887 | 1/1998 |

OTHER PUBLICATIONS

D.G. Rata, F. Casanova, J. Perlo, D. E. Demco, and B. Blümich, "Self-Diffusion Measurements by a Mobile Single-Sided NMR Sensor with Improved Magnetic Filed Gradient," J. Magn. Res, 180 (2006) 229-235.

J. Perlo, F. Casanova, and B. Blüich, Single-Sided Sensor for High-Resolution NMR Spectroscopy, J. Magn, Res., 180 (2006) 274-279.

W. -H. Chang, J. -H. Chen, and L. -P. Hwang, "Single-Sided Mobile NMR with a Halbach Magnet," Magn. Reson. Imag. In Press, 24 (2006) 1095-1102.

A. E. Marble, I. V. Mastikhin, B. G. Coplitts, B. J. Balcom, "A Unilateral Resonance Moisture Sensor for Aerospace Composites," in Proceedings of the Canadian Conference on Electrical and Computer Engineering, May 6-10, Ottawa, On, Canada.

B. Manz, A. Coy, R. Dykstra, C.D. Eccles. M. w. Hunter, B. J. Parkinson and P. T. Callaghan, "A Mobile One-Sided NMR Sensor with a Homogeneous Magnetic Filed: The NMR-MOLE", J. Magn. Res., In Press. 183 (2006) 25-31.

S. Utsuzawa, R. Kemmer, and Y. Nakashima, "Unilateral NMR System by Using a Novel Barrel Shaped Magnet," Proceedings of the 5th Colloquium on Mobile NMR, Sep. 21-23, 2005, Perugia, Italy.

J. Perlo, F. Casanova, and B. Blümich, "Sensitivity Analysis for Single-Sided Sensors," Proceedings of the 6th Colloquium on Mobile NMR, Sep. 6-8, Aachen, Germany.

H. N. Bertram, "Theory of Magnetic Recording, Cambridge:" Cambridge University Press, 1994.

PCT Search Report issued on PCT/CA2007/002115 dated Feb. 22, 2008.

Marble et al. "A Compact Permanent Magnet Array with a Remote Homogeneous Field" Journal of Magnetic Resonance, Academic Press, Orlando, FL. US LNKD-DOI:10.1016/J. JMR, 2007.01.020, vol. 186, No. 1 Apr. 26, 2007, pp. 100-104, XP022056081 ISSN: 1090-7807.

Kleinberg R L et al: "Novel NMR Apparatus for Investigating an External Sample" Journal of Magnetic Resonance, Academic Press, Orlando, FL, US, vol. 97, No. 3, May 1, 1992, pp. 466-485, XP000273747 ISSN: 1090-7807.

Yuly M Pulyer et al: "Generation of Remote Homogeneous Magnetic Fields" IEEE Transactions on Magnetics, IEEE Service Center, New York, NY, US, vol. 38, No. 3, May 1, 2002, XP011075187 ISSM:0018-9464.

Supplementary European Search Report dated Jul. 26, 2010.

Guthausen et al., Analysis of Polymer Materials by Surface NMR via the Mouse, Journal of Magnetic Resonance. 1998, pp. 1-7 130.

Popella et al, Design and Optimization of the Magnetic Circuit of a Mobile Nuclear Magnetic Resonance Device for Magnetic Resonance Imaging, The International Journal for Computation and Mathematics in Electrical and Electronic Engineering, 2001, vol. 20, No. 1, pp. 269-278.

Pederson et al, Application of the NMR-Mouse to Food Emulsions, Journal of Magnetic Resonance, 2003, vol. 165, pp. 49-58.

Popella et al. Object-Oriented Genetic Algorithms for Two-Dimensional Design Optimization of the Magnetic Circuit of a Mobile Magnetic Resonance Device, International Journal of Applied Electromagnetics and Mechanics, 2001/2002, vol. 15, pp. 219-223.

Eidmann, G., et al, The NMR Mouse, A Mobile Universal Surface Explorer, Journal of Magnetic Resonance, Series A, 1996, vol. 122, pp. 104-109.

Glover et al, A Novel High-Gradient Permanent Magnetic for the Profiling of Planar Films and Coatings, Journal of Magnetic Resonance, 1999, vol. 139, pp. 90-97.

Blümich et al, Simple NMR-Mouse with a bar magnet, Concepts in Magnetic Resonance B 15, 2002, pp. 255-261.

Guthausen et al., Soft-matter analysis by the NMR-Mouse, Macromal. Mater. Eng. 276/277, 2000, pp. 25-37.

Nelder et al., A Simplex Method for Function Minimization, The Computer Journal, 1965, vol. 7, pp. 308-313.

McDonald et al., Two-dimensional correlation relaxometry studies of cement pastes performed using a new one-sided NMR magnet, Current and Concrete Research, 2007, vol. 37, pp. 303-309.

Luong et al., Optimal Control Technique for Magnet Design in Inside-Out Nuclear Magnetic Resonance, IEEE Transactions on Magnetics, 2001, vol. 37:2, pp. 1015-1023.

Marble et al., An analytical methodology for magnetic field control in unilateral NMR, Journal of Magnetic Resonance, 2005, vol. 174, pp. 78-87.

Marble et al., A constant gradient unilateral magnet for near-surface MRI profiling, Journal of Magnetic Resonance, 2006, vol. 183, pp. 228-234.

Perlo et al., Profiles with microscopic resolution by single-sided NMR, Journal of Magnetic Resonance, 2005, vol. 176, pp. 64-70.

* cited by examiner

MAGNET ARRAY

This is a National Phase application based on International Application Serial No. PCT/CA2007/002115 filed on Nov. 23, 2007 which claims priority of U.S. Provisional Patent Application No. 60/860,809, filed Nov. 24, 2006.

TECHNICAL FIELD

This application relates to nuclear magnetic resonance in general, and to a compact permanent magnet array suitable for producing a remote magnetic field and process suitable for producing the same, in particular.

BACKGROUND OF THE INVENTION

Early experiments and apparatus designed for nuclear magnetic resonance (NMR) well logging can be found in: [1] "U.S. Pat. No. 3,213,357. R. J. S. Brown, H. C. Torrey, J. Korringa, Earth formation and fluid material investigation by nuclear magnetism relaxation rate determination"; [2] "U.S. Pat. No. 4,350,955. J. A. Jackson, R. K. Cooper, Magnetic resonance apparatus"; [3] "J. A. Jackson, L. J. Burnett, J. F. Harmon, Remote (inside-out) NMR. III. Detection of nuclear magnetic resonance in a remotely produced region of homogeneous magnetic field, J. Magn. Res, 41, 1980, 411-421"; and [4] "R. L. Kleinberg, A. Sezginer, D. D. Griffin, and M. Fukuhara, Novel NMR apparatus for investigating an external sample, J. Magn. Res. 97 (1992) 466-485".

Beginning with these early experiments and apparatus, there has been a continued interest in unilateral NMR (UMR), examples of which can be found in: [5] "J. Perlo, F. Casanova, and B. Blümich, Profiles with microscopic resolution by single-sided NMR, J. Magn. Res. 176 (2005) 64-70"; [6] "P. J. McDonald, J. Mitchell, M. Mulheron, P. S. Aptaker, J.-P. Korb, and L. Monteilhet, Two dimensional correlation relaxometry studies of cement pastes performed using a new one-sided NMR magnet, Cement and Concrete Research, In Press"; [7] "D. G. Rata, F. Casanova, J. Perlo, D. E. Demco, and B. Blümich, Self-diffusion measurements by a mobile single-sided NMR sensor with improved magnetic field gradient, J. Magn. Res, 180 (2006) 229-235"; [8] "J. Perlo, F. Casanova, and B. Blümich, Single-sided sensor for high-resolution NMR spectroscopy, J. Magn. Res., 180 (2006) 274-279"; [9] "G. Eidmann, R. Savelsberg, P. Blümler, and B. Blümich, The NMR MOUSE, a mobile universal surface explorer, J. Magn. Res. A 122 (1996) 104-109"; [10] "B. Blümich, V. Anferov, S. Anferova, M. Klein, R. Fechete, M. Adams, and F. Casanova, Simple NMR-mouse with a bar magnet, Concepts in Magnetic Resonance B 15 (2002) 255-261"; [11] "W.-H. Chang, J.-H. Chen, and L.-P. Hwang, Single-sided mobile NMR with a Halbach magnet, Magn. Reson. Imag., 24 (2006) 1095-1102"; [12] "US Patent Application 2006/0084861, A. Blank, G. Lewkonya, Y. Zur, H. Friedman, and G. Tidhar, Magnet and coil configurations for MRI probes."; [13] "U.S. Pat. No. 5,959,454. M. Westphal, B. Knüttel, Magnet arrangement for and NMR tomography system, in particular for skin and surface examinations."; [14] "U.S. Pat. No. 6,489,872. E. Fukushima, J. A. Jackson, Unilateral magnet having a remote uniform field region for nuclear magnetic resonance."; [15] "A. E. Marble, I. V. Mastikhin, B. G. Coplitts, B. J. Balcom, A unilateral magnetic resonance moisture sensor for aerospace composites, in Proceedings of the Canadian Conference on Electrical and Computer Engineering, May 6-10, Ottawa, ON, Canada."; [16] "B. Manz, A. Coy, R. Dykstra, C. D. Eccles, M. W. Hunter, B. J. Parkinson and P. T. Callaghan, A mobile one-sided NMR sensor with a homogeneous magnetic field: The NMR-MOLE, J. Magn. Res., In Press.183 (2006) 25-31"; [17] "U.S. Pat. No. 5,572,132. Y. M. Pulyer, S. Patz, MRI probe for external imaging"; [18] "S. Utsuzawa, R. Kemmer, and Y. Nakashima, Unilateral NMR system by using a novel barrel shaped magnet, Proceedings of the 5th Colloquium on Mobile NMR, Sep. 21-23, 2005, Perugia, Italy"; and [19] "J. Perlo, F. Casanova, and B. Blümich. Sensitivity analysis for single-sided sensors, Proceedings of the 6th Colloquium on Mobile NMR, Sep. 6-8, 2006, Aachen, Germany".

UMR refers to NMR signal transduction, performed in such a way that the sample volume is external to the measurement apparatus and has the obvious advantage of allowing arbitrarily large samples to be investigated. In modern UMR hardware, permanent magnets are employed to produce the static $B_0$ magnetic field in some remote region.

Several recent designs generate a field with a controlled spatial distribution for experiments such as profiling [5,6], diffusion [7], and spectroscopy [8]. However, most applications still rely on bulk measurements of the magnetization in a 'sensitive volume' defined by the inhomogeneities of $B_0$ and $B_1$, as discussed in: [3,4,9-17].

In the case where a sensitive volume is desired, two distinct classes of instrument exist. While many designs exist producing symmetrical 3D external sensitive volumes, for example a toroid [2], we limit the discussion here to magnets with a sensitive spot above one face. In the first class [9-12], a grossly inhomogeneous $B_0$ field is generated by one or more magnets, and an RF coil is oriented such that $B_1$ and $B_0$ are orthogonal within some region. The $B_0$ gradient along with the excitation bandwidth will define a sensitive volume. The advantages of this method include more compact magnet arrays, stronger $B_0$ fields, and strong gradients which can sensitize measurements to slow molecular motions. Furthermore, many of these designs have $B_0$ directed parallel to the magnet face allowing an ordinary surface coil to be used for excitation and detection, affording both simplicity and sensitivity. Drawbacks include a small spot size, and pronounced diffusive attenuation in liquid samples, both due to the high gradient. By 'ordinary surface coil', we mean a coil made from a simple loop of wire, generating a $B_1$ field directed along the axis of the loop.

The second class of instrument generates a 'sweet spot' at which $B_0$ contains a saddle point and is therefore locally homogeneous [3,4,13-17]. This creates a larger spot for a given excitation bandwidth; the reduced gradient limits diffusive attenuation, facilitating the measurement of liquid samples. The trade-off is that these designs generally operate at a lower field as the saddle point is obtained by field cancellation.

SUMMARY

According to one aspect of the present invention, there is provided: a magnet array suitable for use in nuclear magnetic resonance (NMR) signal transduction, comprising: (a) two separated magnets, magnetized along a substantially same magnetization direction, each of the two separated magnets aligned such that one pole in one magnet is facing an other pole having an opposite polarity in the other magnet so as to define an axis in the separation between the two magnets, the two separated magnets producing a field with a local maximum which is substantially parallel to the magnetization direction of the two separated magnets, the local maximum positioned between the two separated magnets and offset from the axis in a direction perpendicular to the axis; and (b) a third magnet, magnetized along the substantially same magnetization direction of the two separated magnets, the third magnet positioned in the separation between the two separated magnets, the third magnet aligned to have each one of its poles facing one pole of the two separated magnets which has opposite polarity.

According to another aspect of the present invention, there is provided: a process suitable for producing a magnet array, the method comprising the steps of: (a) providing two separated magnets, magnetized along a substantially same magnetization direction, each of the two separated magnets aligned such that one pole in one magnet is facing an other pole having an opposite polarity in the other magnet so as to define an axis in the separation between the two magnets, the two separated magnets producing a field with a local maximum which is substantially parallel to the magnetization direction of the two separated magnets, the local maximum positioned between the two separated magnets and offset from the axis in a direction perpendicular to the axis; and (b) positioning a third magnet between said two separated magnets, the third magnet magnetized along the substantially same magnetization direction of the two separated magnets, the third magnet aligned to have each one of its poles facing one pole of the two separated magnets which has opposite polarity.

According to yet another aspect of the present invention, there is provided: a nuclear magnetic resonance apparatus comprising: (a) a dynamic field generator; (b) an RF supply module connected to the a dynamic field generator suitable for generating an RF signal compatible with nuclear magnetic resonance; (c) a detection module connected to the at least one dynamic field generator for detecting an RF signal compatible with nuclear magnetic resonance; (d) and a magnet array suitable for use in nuclear magnetic resonance (NMR) signal transduction, the magnet array comprising: (i) two separated magnets, magnetized along a substantially same magnetization direction, each of the two separated magnets aligned such that one pole in one magnet is facing an other pole having an opposite polarity in the other magnet so as to define an axis in the separation between the two magnets, the two separated magnets producing a field with a local maximum which is substantially parallel to the magnetization direction of the two separated magnets, the local maximum positioned between the two separated magnets and offset from the axis in a direction perpendicular to the axis; and (ii) a third magnet, magnetized along the substantially same magnetization direction of the two separated magnets, the third magnet positioned in the separation between the two separated magnets, the third magnet aligned to have each one of its poles facing one pole of the two separated magnets which has opposite polarity.

According to still yet another aspect of the present invention, there is provided: a method of using a magnet array suitable for use in nuclear magnetic resonance (NMR) signal transduction, the magnet array comprising: (a) two separated magnets, magnetized along a substantially same magnetization direction, each of the two separated magnets aligned such that one pole in one magnet is facing an other pole having an opposite polarity in the other magnet so as to define an axis in the separation between the two magnets, the two separated magnets producing a field with a local maximum which is substantially parallel to the magnetization direction of the two separated magnets, the local maximum positioned between the two separated magnets and offset from the axis in a direction perpendicular to the axis; and (b) a third magnet, magnetized along the substantially same magnetization direction of the two separated magnets, the third magnet positioned in the separation between the two separated magnets, the third magnet aligned to have each one of its poles facing one pole of the two separated magnets which has opposite polarity; the method comprising the step of manipulating the third magnet so that its centre is offset from the axis at a point on a line extending perpendicularly from the axis to the local maximum.

Other aspects and features of the present invention will become apparent to those ordinarily skilled in the art upon review of the following description of specific embodiments of a compact permanent magnet array suitable for producing a remote magnetic field and process suitable for producing the same in conjunction with the accompanying drawing figures.

BRIEF DESCRIPTION OF THE DRAWINGS

Embodiments of the present invention will now be described, by way of example only, with reference to the accompanying drawing figures, wherein.

Like reference numerals are used in different figures to denote similar elements.

DETAILED DESCRIPTION OF THE DRAWINGS

Figure 1:
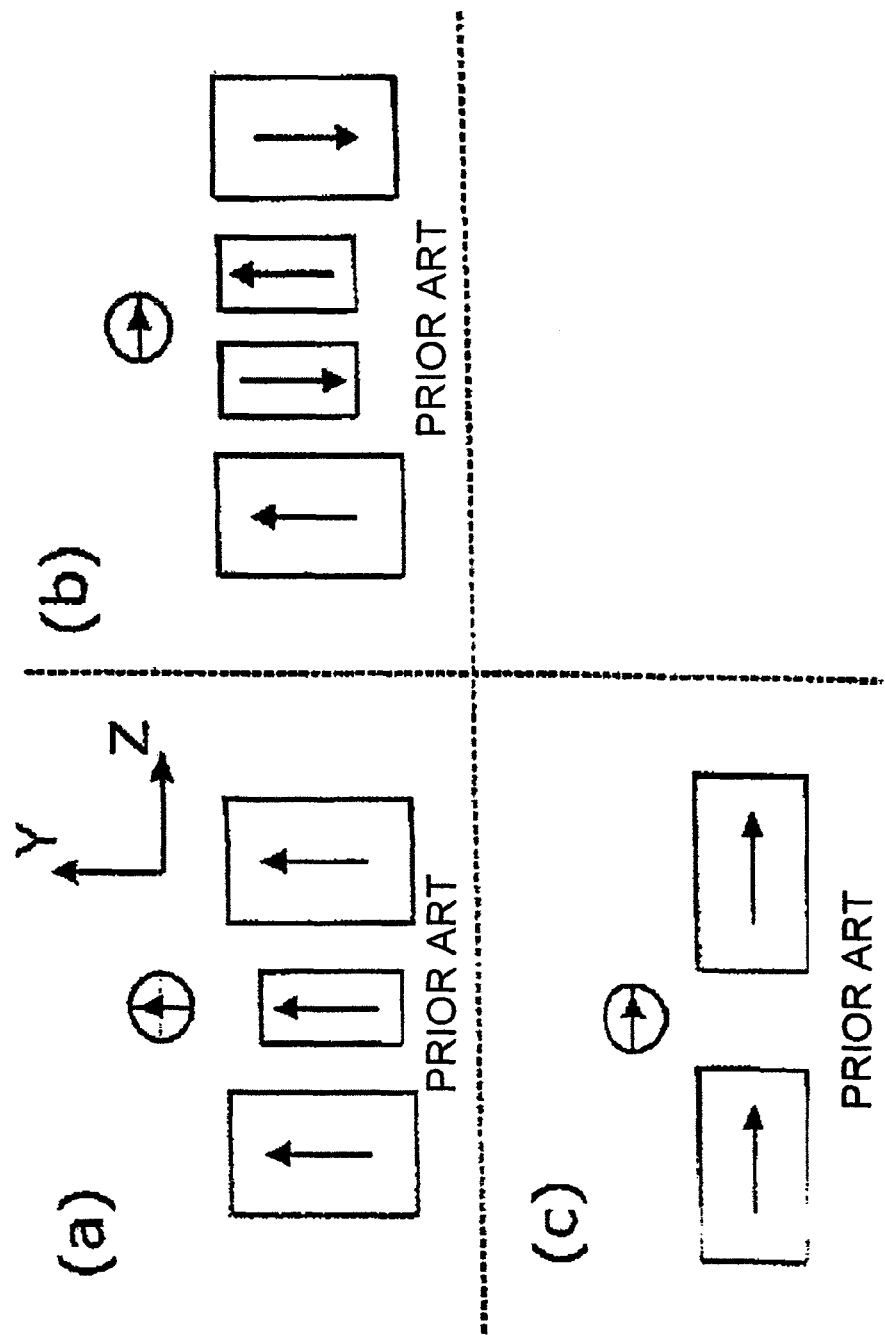
FIG. 1 illustrates prior-art sweet spot magnet array configurations.

Referring to the drawings, FIG. 1 illustrates prior-art sweet spot magnet array configurations. Rectangles denote permanent magnets with their magnetization direction indicated by the arrows. Circles indicate approximate location of the sensitive sweet spot, with the arrows showing the magnetic field direction. Most sweet spot magnets reported in the literature have a $B_0$ field directed orthogonal to the magnet face [3,4, 13,16,17]. In a 2D plane, two magnets with the same orientation can be arranged to give a saddle point; a third magnet placed between them can zero the second spatial derivative of the field in the depth direction, creating a relatively homogeneous spot. This is typified by designs such as Kleinberg's well logging magnet [4] and Fukushima's barrel magnet [14], and is illustrated schematically in FIG. 1(a). While this leads to a compact, simple design, one drawback is that an ordinary surface coil cannot be used as its field will be parallel to $B_0$. Instead, more elaborate, and generally less sensitive coils must be employed [18]. It was recently noted [19] that the advantages of the improved B0 homogeneity of a sweet spot magnet compared to a high-gradient design such as the NMR-MOUSE [9] are negated by the elimination of an ordinary surface coil from the measurement.

There have been sweet spot magnets designed with $B_0$ parallel to their surface to allow the use of an ordinary surface coil [8,15]. In these cases, four magnets, arranged in alternating orientations as shown in FIG. 1(b) have been used, the net effect being a cancellation of the inhomogeneity of the outer pair with that of the inner pair. A disadvantage of this configuration is that the magnet array must in general be large relative to the sensitive volume, in order to give the $B_0$ field the space necessary to reorient itself from vertical (over the magnets) to horizontal (in the sweet spot). Furthermore, we have found in practice that although it is straightforward to generate a saddle point with this design, zeroing the second spatial derivative of $B_0$ may incur severe array size and field strength penalties. The field from previously reported designs of this type rapidly becomes inhomogeneous away from the saddle point.

Pulyer and Patz [17] have proposed a design in which two axially magnetized and axially oriented magnets are spaced in such a way as to generate a saddle point in the field above them. A diagram of this configuration is given in FIG. 1(c). The advantage of this design is that a saddle point can be generated from a relatively compact array (as the field is already oriented in the correct direction over the magnets) and an ordinary surface coil may be employed for the measurement. In this arrangement, only the first field derivative can in general be made zero.

Figure 2:
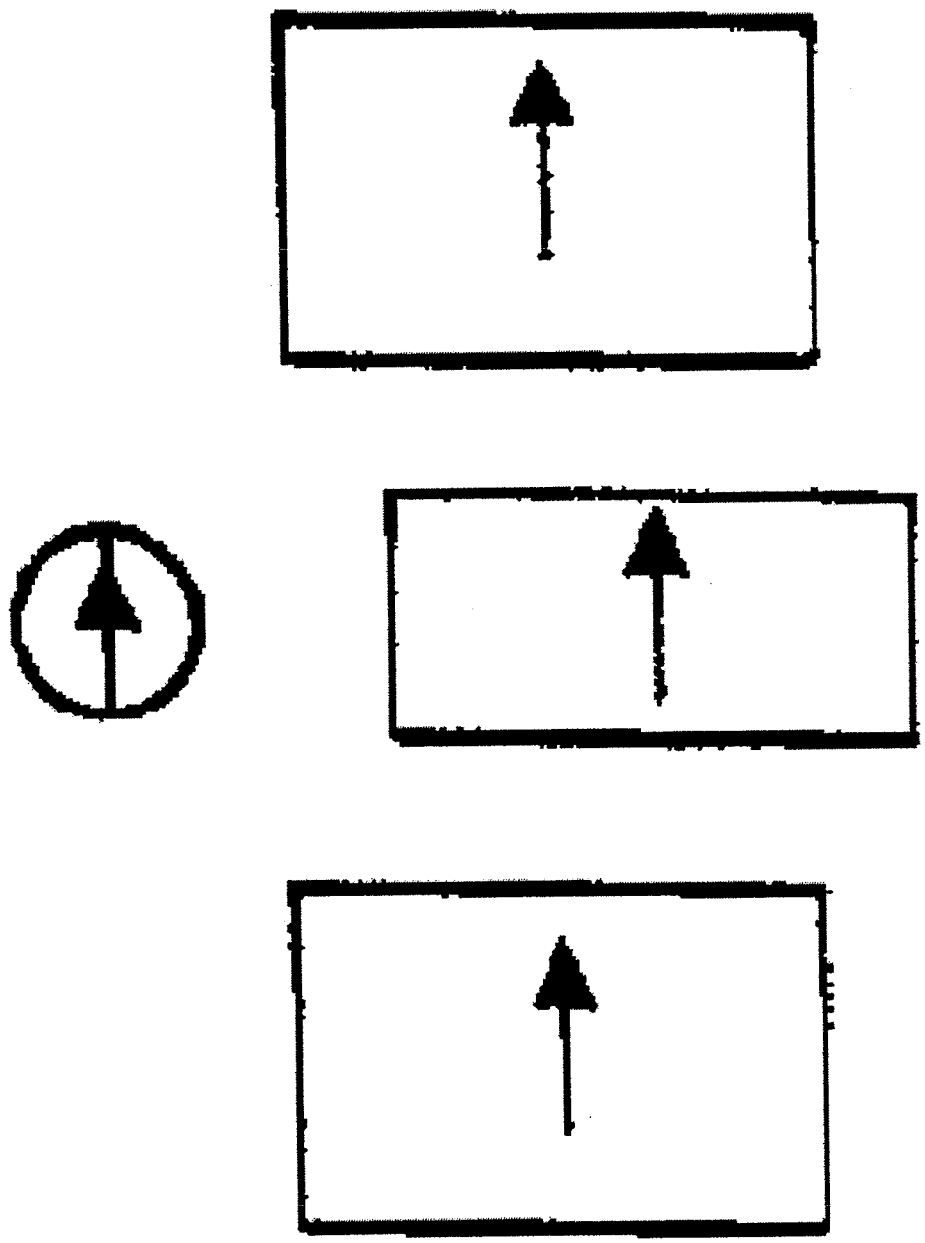
FIG. 2 illustrates an example sweet spot magnet array configuration provided in accordance with one embodiment of the present invention.

Referring now to FIG. 2, FIG. 2 illustrates an example sweet spot magnet array configuration provided in accordance with one embodiment of the present invention. Rectangles denote permanent magnets with their magnetization direction indicated by the arrows. Circles indicate approximate location of the sensitive sweet spot, with the arrows showing the magnetic field direction. The example of FIG. 2 exploits the benefits of Pulyer's design [17] and the configuration of FIG. 1(a) to develop a simple magnet arrangement in which the first and second spatial derivatives of $B_0$ can be zeroed to give a large, homogeneous spot, with the field oriented parallel to the magnet surface. This provides all of the advantages of previous sweet spot designs with the sensitivity and simplicity offered by an ordinary surface coil. Because the field above the magnets is already parallel to their surface, the design is naturally more compact. The design has the added advantage that all the magnets are oriented along the same axis, a safe, low energy configuration in comparison to the design shown in FIG. 1(a), wherein strong repulsive forces exist between the magnets, creating a potential safety problem.

In what follows, we briefly outline exemplary steps provided in accordance with one embodiment of the present invention for enabling one of ordinary skill in the art to obtain advantageous embodiments of the same class as the example magnet arrangement shown in FIG. 1, and show field plots from a fabricated device. Sample experimental results are presented to give an idea of the sensitivity of the resulting example magnet arrangement.

Embodiment of the Process and Example Product of Process

Magnetic Field Calculation

We begin by deriving a simple equation for the magnetic field due to a bar magnet. While this calculation can be found in the literature ([20] "H. N. Bertram, Theory of Magnetic Recording, Cambridge: Cambridge University Press, 1994"), it is somewhat obscure, and may be of interest to those designing UMR arrays with permanent magnets.

Figure 3:
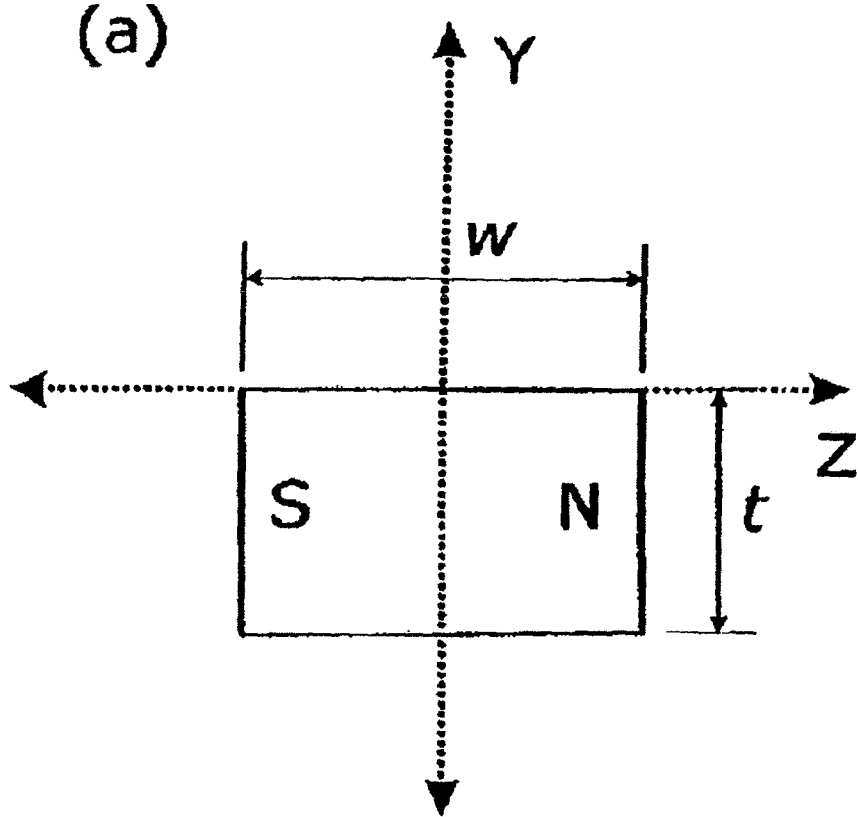
FIG. 3 illustrates magnet positioning and orientation selected to use the field along the sides of the magnets for calculations so as to approximate a permanent magnet as two sheets of thin wires.
Figure 3:
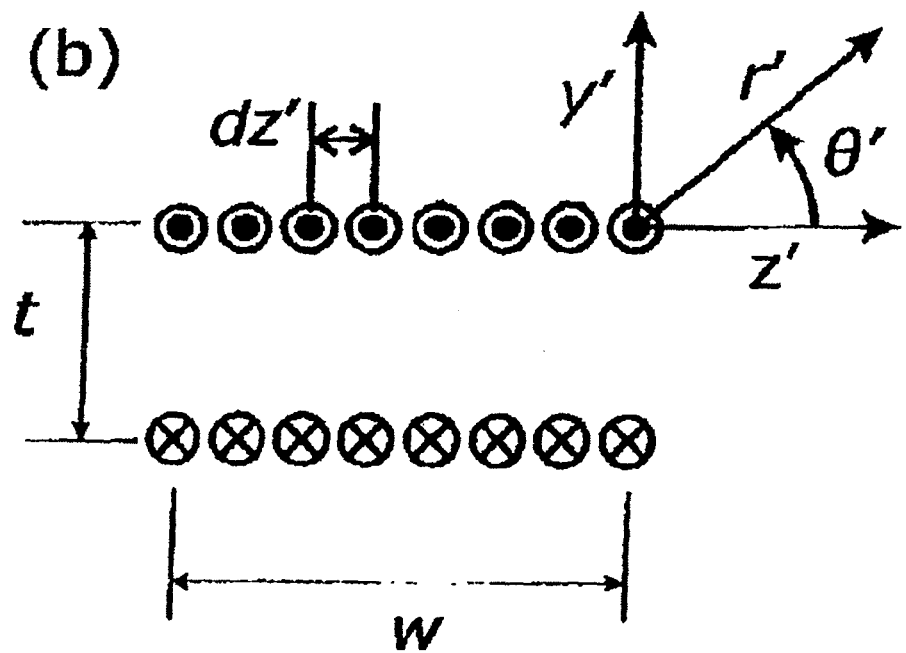

FIG. 3 illustrates magnet positioning and orientation selected to use the field along the sides of the magnets for calculations so as to approximate a permanent magnet as two sheets of thin wires. FIG. 3(a) illustrates a magnet which is magnetized along $\hat{z}$ and positioned with its upper surface at the origin. The width of the magnet is w, and its thickness, t. If the magnet is assumed to be infinitely long in the depth (x) direction, it can be represented by two sheets of current I located at its upper and lower surfaces. From the right hand rule, the current flows out of the page on the top surface and into the page on the bottom.

FIG. 3(b) illustrates that the sheets of current of FIG. 3(a) can be divided into infinitesimal line current elements of width dz'. The magnetic field due to such a current is well known:

$$\vec{B}' = \frac{\mu_0 i}{2\pi r'} \hat{\theta}' \qquad (1)$$

where i=Idz' is the current in each wire, r' is the distance from the wire to the observation point and $\hat{\theta}'=-\sin\theta'\hat{z}'+\cos\theta'\hat{y}'$ is the unit normal in polar coordinates. Converting to Cartesian coordinates, the total field due to the current in the upper sheet can be calculated by integration giving $$\vec{B}_{top}(z,y) = K\left[-\int_{-w/2}^{w/2} \frac{y}{(z-z')^2+y^2}dz'\hat{z} + \int_{-w/2}^{w/2} \frac{z-z'}{(z-z')^2+y^2}dz'\hat{y}\right] \qquad (2)$$

where $K=\mu_0 I/(2\pi)$. Integrating, and adding $\vec{B}_{bottom}=-\vec{B}_{top}(z,y+t)$ to represent the bottom sheet gives the total field from the magnet $$\vec{B}(z,y) = K\left[-\tan^{-1}\left(\frac{z-w/2}{y}\right)+\tan^{-1}\left(\frac{z+w/2}{y}\right)+ \right. \qquad (3)$$
$$\left. \tan^{-1}\left(\frac{z-w/2}{y+t}\right)-\tan^{-1}\left(\frac{z+w/2}{y+t}\right)\right]\hat{z} +$$
$$\frac{K}{2}\left[\log\left(\frac{y^2+(z+w/2)^2}{y^2+(z-w/2)^2}\right)-\log\left(\frac{(y+t)^2+(z+w/2)^2}{(y+t)^2+(z-w/2)^2}\right)\right]\hat{y}.$$

We have found that this expression agrees almost exactly with 2D finite element simulations of a single, uniformly magnetized permanent magnet. The field from many permanent magnets can be calculated by superposition. This calculation assumes infinitely long magnets, and does not take into account inhomogeneities in the magnetization, or saturation effects from magnets in close proximity. As such, it will never be able to exactly calculate the field from a real magnet array. However, we have found that it can serve as a simple and reasonably accurate guideline for magnet array design.

Three Magnet Configuration

As pointed out by Fukushima and Jackson [14], two separated magnets, magnetized along the same direction will produce a field with a local maximum centered above and between them. According to a second step of one embodiment of the process, the position of a third magnet centered between the first two is adjusted such that its field, which decays with distance, adds to the increasing field below the saddle point in order to generate a field which has its first and second spatial derivatives with respect to y equal to zero. According to an optional step, it is also possible to introduce a controlled y-gradient in the field by varying the position of the central magnet. While previous designs rely on the field above the poles of the magnets, advantageously embodiments of the invention use the field along the sides of the magnets.

Figure 4:
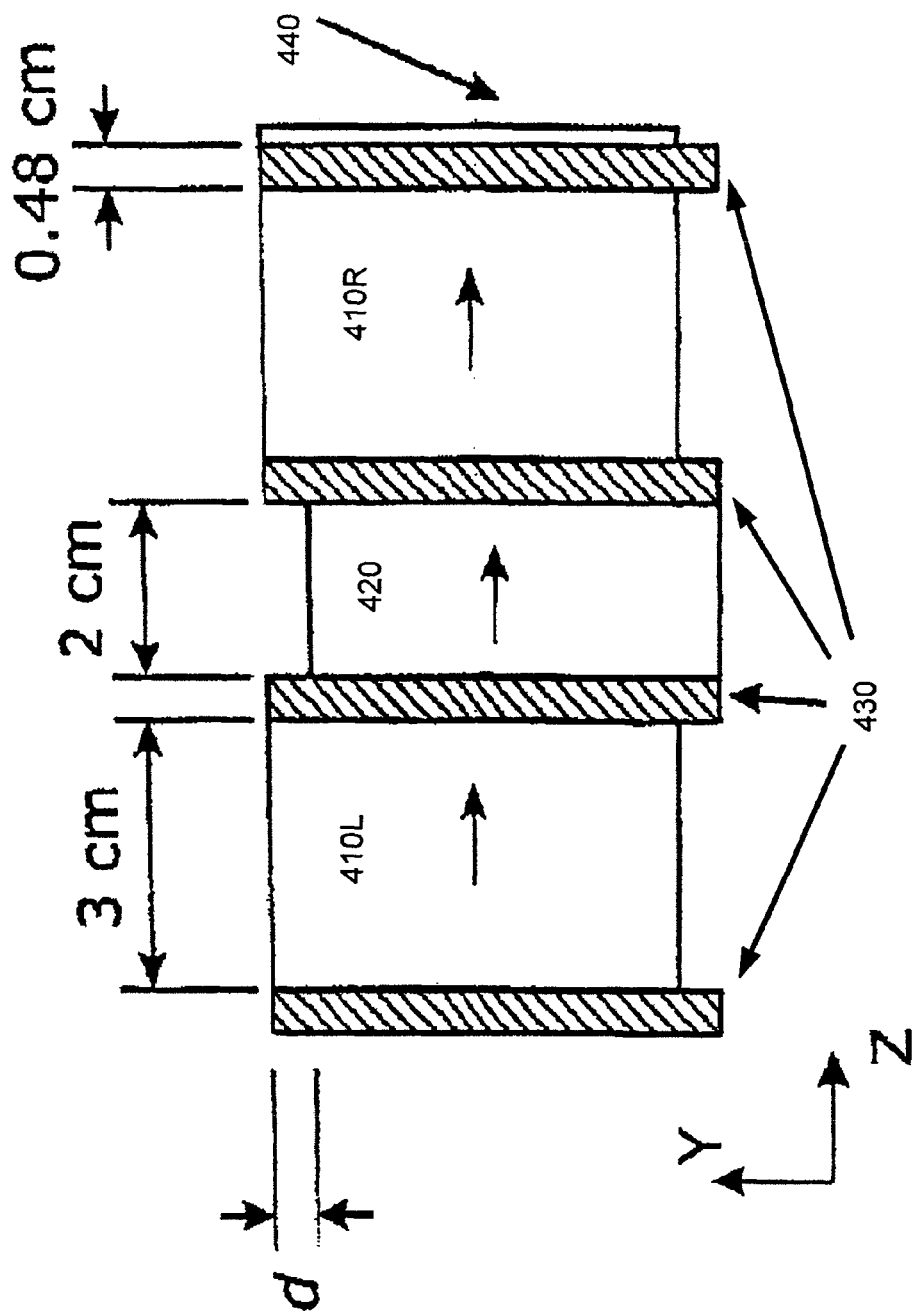
FIG. 4 illustrates an example three magnet array provided in accordance with an embodiment of the present invention.

Referring to FIG. 4, FIG. 4 illustrates an example three magnet array provided in accordance with an embodiment of the present invention. The example embodiment includes three magnets, all magnetized along z. The magnets 410L, 420 and 410R, with sizes and direction of magnetization shown, are spaced apart with aluminium spacers 430. An optional piece of steel 440 is used to compensate for the lower magnetization of the rightmost magnet 410R. The magnets 410L, 420, and 410R all have t=5 cm, the outer pair of magnets 410L and 410R have w=3 cm while the inner magnet 420 has w=2 cm. The spacing between each magnet was set to 4.76 mm (3/16") in order to accommodate stock aluminium as a spacer 430. The inner magnet 420 is offset a distance d below the outer magnets 410L and 410R in order to give the appropriate field. Using Eq. (3), it was calculated that for a central magnet offset by d=4.8 mm, the first and second field derivatives would be zero at a point 1.08 cm above the outer magnets.

Results Enabled by the Embodiments of the Process and Product

Field Measurements

Magnets of the sizes given above, and 10 cm long in the 'infinite' direction, were purchased from the Yuxiang Magnetic Materials Ind. Co., Ltd (Xiamen, China). The magnets were NdFeB with a specified remanence of ~1.3 T. Due to manufacturing tolerances, the purchased magnets had a variation in surface field of ~8% between the pair of outer magnets. The field of the central magnet was somewhere in between the two values of the outer magnets. A variation on this scale was anticipated, and a frame was designed for the magnets such that the offset d of the center magnet could be varied in order to achieve the desired field. To assist in correcting the field, two pieces of scrap steel, each measuring 5 cm by 10 cm and ~1 mm thick were placed side by side outside the frame next to the magnet with the lower field. These have the effect of shifting the magnetic flux lines to that side and can reduce the asymmetry in the field. It was found that with this configuration, the first and second derivatives of the field can be approximately zeroed at a point about 1.05 cm above the face of the magnets with the offset d of the central magnet equal to 5 mm. These numbers correspond very well with the calculated magnet positions.

Magnetic field measurements were made with a Lakeshore 460 3-axis Hall probe and a computer controlled 3-axis position system.

Figure 5:
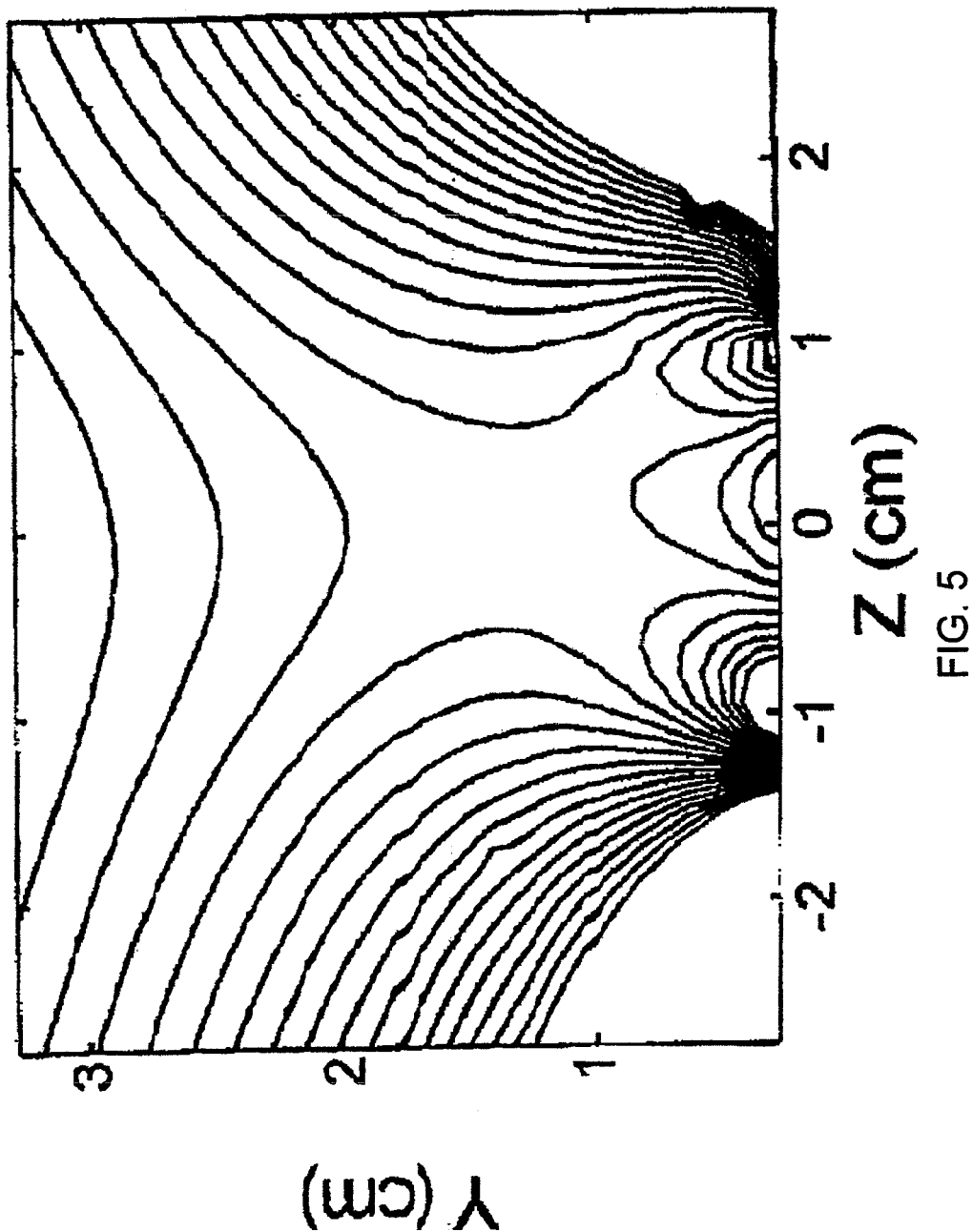
FIG. 5 shows a contour plot of the magnetic field magnitude over the example array of FIG. 4.

FIG. 5 shows a contour plot of the magnetic field magnitude over the example array of FIG. 4. The position y=0 corresponds to the upper surface of the outer magnets. A slight asymmetry is noted for larger values of |z| due to the unequal magnetizations of the outer magnets, however the field over the center is reasonably symmetric. A saddle point is observed in the central region over the magnet.

Figure 6:
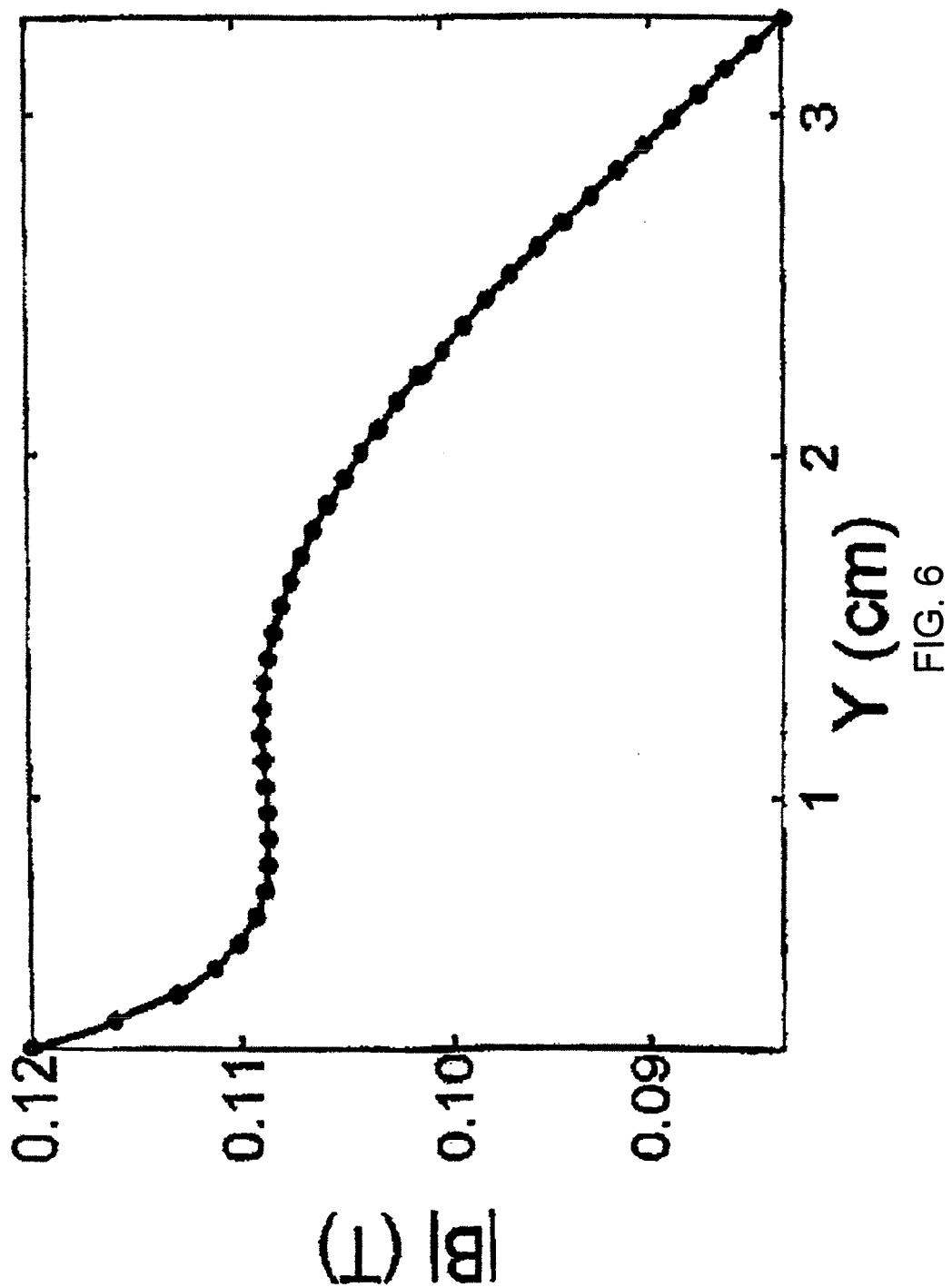
FIG. 6 plots the field magnitude as a function of z over the center of the magnets of the example array of FIG. 4.

FIG. 6 plots the field magnitude as a function of z over the center of the magnets of the example array of FIG. 4. The approximately flat region occurring around 1 cm from the magnet surface corresponds to the sensitive volume. There is a slight upward trend in the field strength at the center of the sensitive spot, but the field, which is nominally 0.109 T, remains within a 0.25 mT range over a region more than 5 mm deep.

NMR Measurements

We present several measurements here in order to demonstrate the sensitivity of the instrument. Measurements used an inductively coupled ordinary surface coil, 1.5 cm in diameter, and tuned to 4.646 MHz. The coil was positioned ~5 mm above the surface of the outer magnets. Experiments were conducted with a Bruker Minispec console, modified to include an external Mitec preamplifier and lumped element duplexer. The sample was a bottle of commercially available fish oil, larger than the sensitive volume of the instrument.

Figure 7:
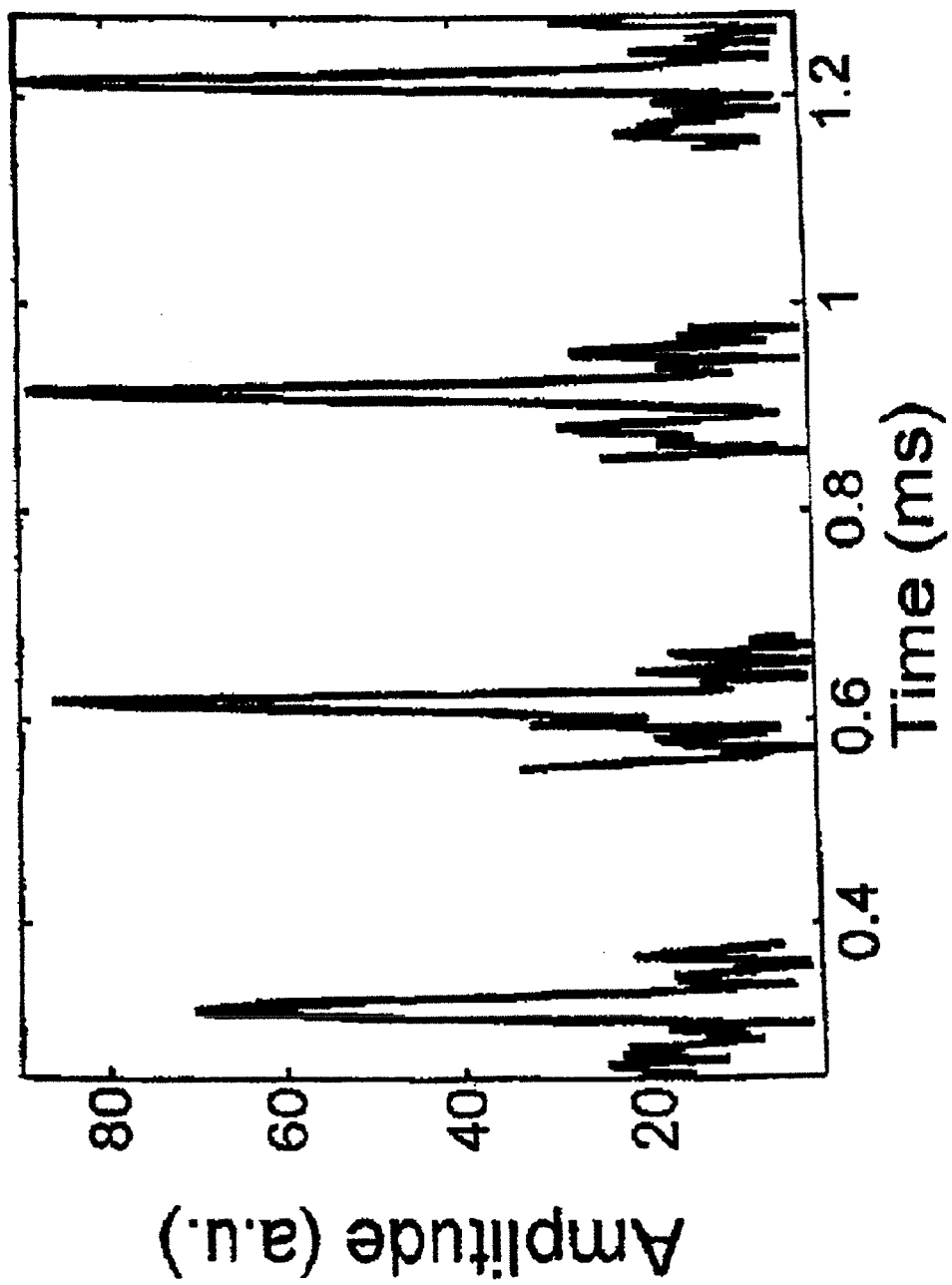
FIG. 7 illustrates four echoes, acquired using a CPMG sequence in a single scan, using the array shown in FIG. 4.

FIG. 7 illustrates four echoes, acquired using a CPMG sequence in a single scan, using the array shown in FIG. 4. As is common practice when working with inhomogeneous fields, the lengths of the 90° and 180° pulses were kept equal, and the flip angle adjusted by changing the pulse power; this ensures that the excitation bandwidth remains constant. The echoes are clearly resolved. The experimental time of just over 1 ms is much shorter than the sample $T_2$ and no attenuation is observed. The magnitude of the first echo is lower than that of subsequent echoes, a common phenomenon in inhomogeneous fields [4].

Figure 8:
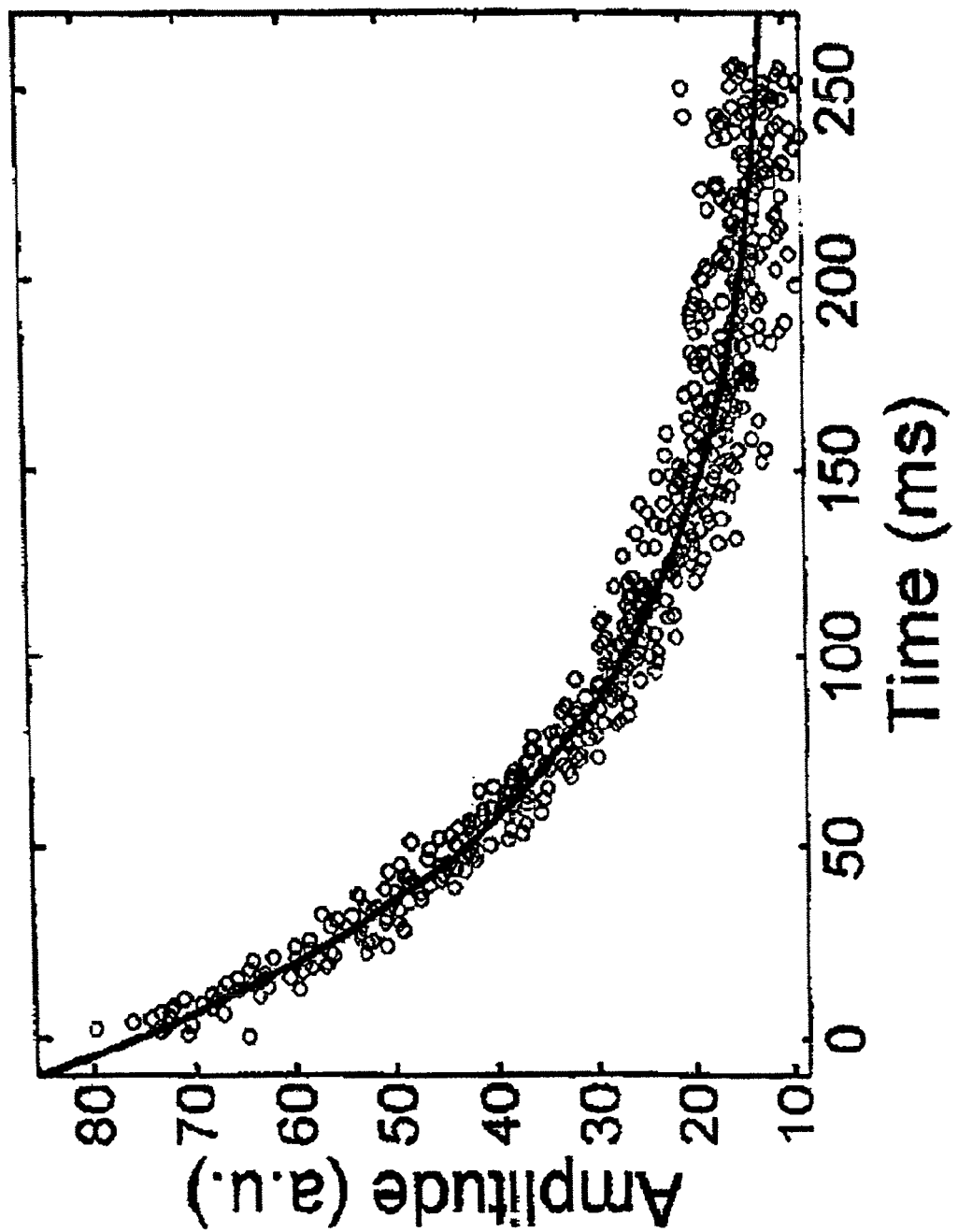
FIG. 8 shows a CPMG decay, measured with 8 signal averages, using the array shown in FIG. 4.

FIG. 8 shows a CPMG decay, measured with 8 signal averages, using the array shown in FIG. 4. In both FIGS. 7 and 8, relatively high quality data is obtained in a minimal experimental time, an advantageous feature that is important for on-line measurements.

We have presented embodiments of a single sided magnet array generating a homogeneous field in an external volume and embodiments of a process suitable to provide the same. While designs with these general characteristic are known, the embodiments have $B_0$ oriented parallel to the face of the magnets in the array, allowing a simple circular surface coil to be used for signal transduction. This feature increases the sensitivity of the instrument dramatically compared to designs that require special surface coils to produce a z-directed RF field.

The example magnet array measures 10 cm by 11.5 cm by 6 cm, and weighs ~5 kg. Despite being much smaller than our previous 4-magnet designs with $B_0$ oriented along z, [15], the optimized field makes the instrument far more sensitive.

Figure 9:
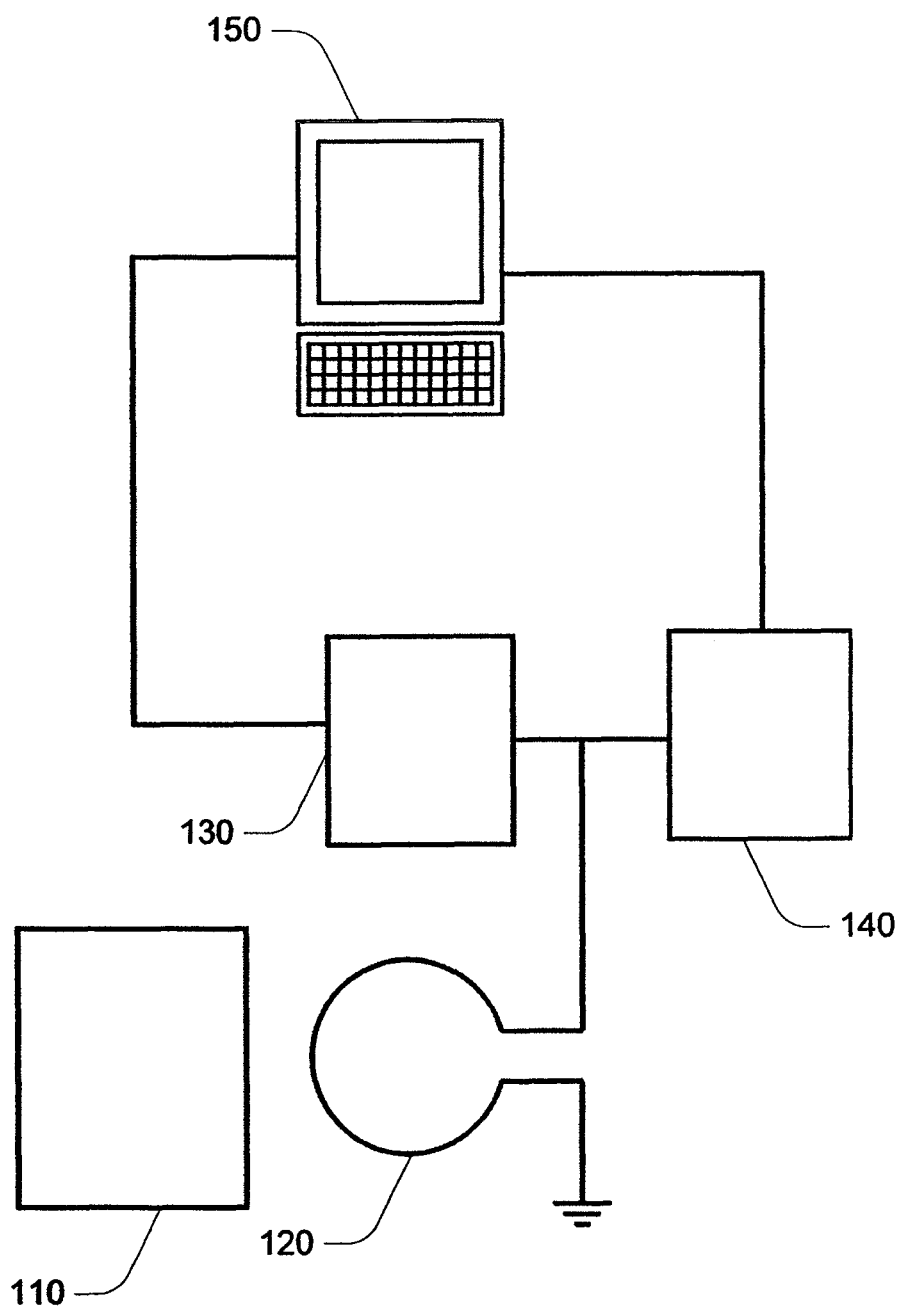
FIG. 9 is a block diagram of an embodiment of and NMR apparatus provided in accordance with the present invention.

FIG. 9 is a block diagram of an embodiment of and NMR apparatus provided in accordance with the present invention. The magnet array 110 produces a suitable static magnetic field in a region of interest. The dynamic field generator 120 generates a dynamic radiofrequency magnetic field in the region of interest. The RF supply module 130 is connected to the dynamic field generator and supplies an RF signal compatible with nuclear magnetic resonance to the dynamic field generator. The detection module 140 detects nuclear magnetic resonance signals induced in the dynamic field generator. The RF supply module is controlled with a computer 150, and the signals detected by the detection module are recorded and processed on the computer.

The above-described embodiments of the present invention are intended to be examples only. Those of skill in the art may effect alterations, modifications and variations to the particular embodiments without departing from the scope of the invention, which is set forth in the claims.

What is claimed is:

1. A magnet array suitable for use in nuclear magnetic resonance (NMR) signal transduction, comprising:
   (a) two separated magnets, magnetized along a substantially same magnetization direction, each of the two separated magnets aligned such that one pole in one magnet is facing another pole so as to define an axis in the separation between the two magnets, the two separated magnets producing a field with a local maximum which is substantially parallel to the magnetization direction of the two separated magnets, the local maximum positioned between the two separated magnets and offset from the axis in a direction perpendicular to the axis; and (b) a third magnet, magnetized along the substantially same magnetization direction of the two separated magnets, the third magnet positioned in the separation between the two separated magnets, the third magnet aligned to have each one of its poles facing one pole of the two separated magnets.

2. The magnet array as recited in claim 1, further including a radiofrequency magnetic field generator.

3. The magnet array as recited in claim 1, wherein the third magnet is positioned relative to the two separated magnets so as to introduce a gradient in the field in a direction substantially perpendicular to the axis.

4. The magnet array as recited in claim 1, wherein the two separated magnets are arranged symmetrically about the separation.

5. The magnet array as recited in claim 1, wherein the two separated magnets are substantially identical.

6. The magnet array as recited in claim 1, wherein the third magnet is positioned in the separation between the two magnets so that its centre is offset from the axis at a point on a line extending perpendicularly from the axis to the local maximum.

7. The magnet array as recited in claim 6, wherein the centre of the third magnet is substantially equidistant from the two separated magnets.

8. The magnet array as recited in claim 1, wherein the third magnet is positioned relative to the two separated magnets such that the third magnet produces so as to generate a resultant field selected from the group consisting of: a resultant field which is substantially parallel to the magnetization direction of the two separated magnets that adds to the increasing field between the local maximum point produced by the two separated magnets and the axis in the separation between the two magnets, a resultant field which has a spatial derivative taken in a direction which is perpendicular to the axis which is substantially equal to zero at a point of interest, and a resultant field which has a spatial derivative taken in a direction which is perpendicular to the axis which is substantially not equal to zero at a point of interest.

9. The magnet array as recited in claim 1, further comprising a spacer positioned between at least one of the two separated magnets and the third magnet.

10. The magnet array as recited in claim 9, wherein the spacer is made of a material which has a permeability that is substantially equal to unity.

11. The magnet array as recited in claim 1, further comprising a piece of high permeability material positioned adjacent to one of the two separated magnets so as to compensate for a lower magnetization of the one of the two separated magnets.

12. A process suitable for producing a magnet array, the method comprising the steps of:

(a) providing two separated magnets, magnetized along a substantially same magnetization direction, each of the two separated magnets aligned such that one pole in one magnet is facing another pole so as to define an axis in the separation between the two magnets, the two separated magnets producing a field with a local maximum which is substantially parallel to the magnetization direction of the two separated magnets, the local maximum positioned between the two separated magnets and offset from the axis in a direction perpendicular to the axis; and (b) positioning a third magnet between said two separated magnets, the third magnet magnetized along the substantially same magnetization direction of the two separated magnets, the third magnet aligned to have each one of its poles facing one pole of the two separated magnets.

13. The process as recited in claim 12, wherein the step of providing two separated magnets is comprises the act of arranging the two separated magnets symmetrically about the separation.

14. The process as recited in claim 12, wherein the two separated magnets are substantially identical.

15. The process as recited in claim 12, wherein the positioning step comprises the an act of selected from the group consisting of: positioning the third magnet so that its centre is offset from the axis at a point on a line extending perpendicularly from the axis to the local maximum, positioning the centre of the third magnet at a point which is substantially equidistant from the two separated magnets, positioning the third magnet relative to the two separated magnets so as to generate a resultant field which is substantially parallel to the magnetization direction of the two separated magnets that adds to the increasing field between the local maximum point produced by the two separated magnets and the axis in the separation between the two magnets, positioning the third magnet relative to the two separated magnets so as to generate a resultant field which has a spatial derivative taken in a direction which is perpendicular to the axis which is substantially equal to zero at a point of interest, positioning the third magnet relative to the two separated magnets so as to generate a resultant field which has a spatial derivative taken in a direction which is perpendicular to the axis which is substantially not equal to zero at a point of interest, and positioning the third magnet relative to the two separated magnets so as to introduce a gradient in the field in a direction substantially perpendicular to the axis.

16. The process as recited in claim 12, further comprising the step of positioning a spacer between at least one of the two separated magnets and the third magnet.

17. The process as recited in claim 16, wherein the spacer is made of low permeability material.

18. The process as recited in claim 12, wherein the spatial derivative that is substantially equal to zero is the first spatial derivative or the second spatial derivative.

19. A nuclear magnetic resonance apparatus comprising:

(a) a dynamic field generator;

(b) an RF supply module connected to the a dynamic field generator suitable for generating an RF signal compatible with nuclear magnetic resonance;

(c) a detection module connected to the at least one dynamic field generator for detecting an RF signal compatible with nuclear magnetic resonance;

(d) and a magnet array suitable for use in nuclear magnetic resonance (NMR) signal transduction, the magnet array comprising:

(i) two separated magnets, magnetized along a substantially same magnetization direction, each of the two separated magnets aligned such that one pole in one magnet is facing another pole so as to define an axis in the separation between the two magnets, the two separated magnets producing a field with a local maximum which is substantially parallel to the magnetization direction of the two separated magnets, the local maximum positioned between the two separated magnets and offset from the axis in a direction perpendicular to the axis; and (ii) a third magnet, magnetized along the substantially same magnetization direction of the two separated magnets, the third magnet positioned in the separation between the two separated magnets, the third magnet aligned to have each one of its poles facing one pole of the two separated magnets.

20. The nuclear magnetic resonance apparatus as recited in claim 19 wherein the two separated magnets are substantially identical.

* * * * *